United States Patent [19]

Schrock, Jr.

[11] Patent Number: 4,699,296

[45] Date of Patent: Oct. 13, 1987

[54] DISPENSING DEVICE FOR EXTERNAL OR INTRAVENOUS INJECTION OF FLUIDS INTO A PATIENT

[76] Inventor: John Schrock, Jr., 1001 Cynthia, McAllen, Tex. 78503

[21] Appl. No.: 825,980

[22] Filed: Feb. 4, 1986

[51] Int. Cl.[4] .......................... B67B 7/52; B67D 5/38
[52] U.S. Cl. ...................................... 222/85; 222/155; 222/181; 222/189; 222/478; 248/318; 604/260; 604/414
[58] Field of Search .................... 222/80, 81, 83.5, 85, 222/86, 88, 155, 105, 107, 180, 181, 183, 185, 478, 479, 481, 41, 44, 47, 49, 50, 189, 190; 604/405, 407, 408, 411, 414, 246, 257, 260; 248/318, 311.2

[56] References Cited

U.S. PATENT DOCUMENTS

| | | | |
|---|---|---|---|
| 803,469 | 10/1905 | Cilley et al. | 222/155 |
| 1,417,141 | 5/1922 | Carter | 222/85 |
| 2,218,285 | 10/1940 | Jellik, Jr. | 222/81 |
| 2,816,692 | 12/1957 | Schade | 222/155 X |
| 3,229,678 | 1/1966 | Anspach | 222/155 X |
| 3,239,104 | 3/1966 | Scholle | 222/88 X |
| 3,288,332 | 11/1966 | Etter et al. | 222/181 X |
| 3,880,311 | 4/1975 | McPhee | 604/260 X |
| 4,257,748 | 3/1981 | Ives et al. | 222/155 X |

Primary Examiner—Joseph J. Rolla
Assistant Examiner—Kevin P. Shaver
Attorney, Agent, or Firm—Cushman, Darby & Cushman

[57] ABSTRACT

A dispensing device formed of a cradle for receiving a brick pack. The cradle includes a pair of apertures located near the bottom and top of the cradle. The dispensing member has a pair of spikes at each end thereof which pass through the pair of apertures in the cradle and pierce the brick pack contained by the cradle. The spikes each have openings therein which communicate with the hollow interior of the dispenser to permit the flow of fluid therein. At the top end of the dispenser is a vent opening having a filter therein for permitting the ingress of air. At the bottom of the dispenser is an opening for permitting the egress of fluid from the brick pack and the dispenser. Preferably the dispenser has a graduated scale to indicate the level of fluid in the brick pack.

11 Claims, 4 Drawing Figures

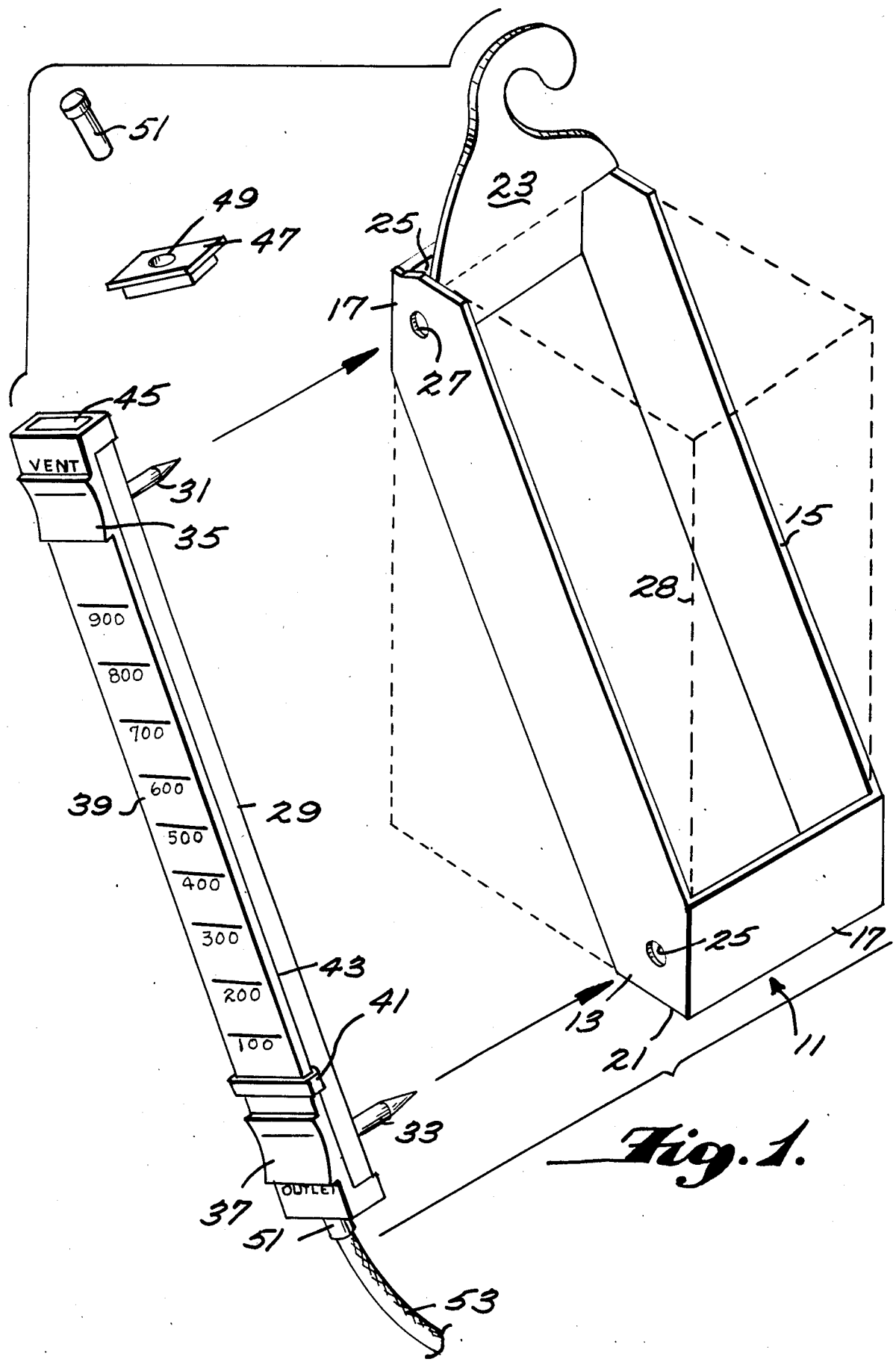

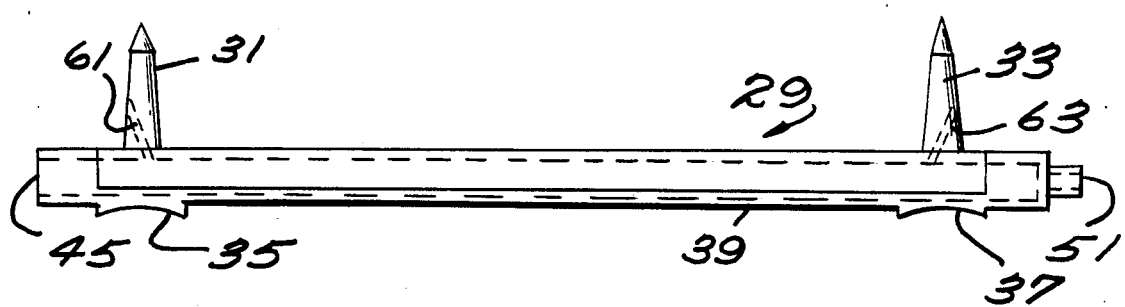
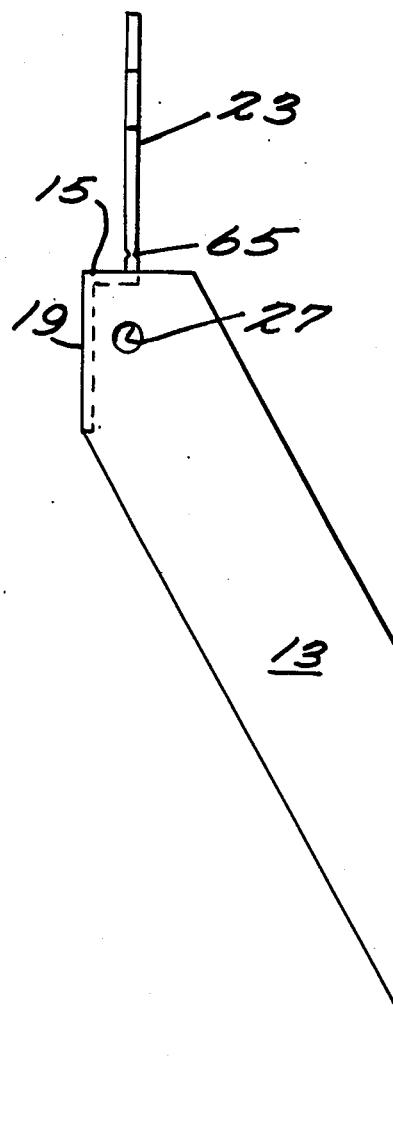
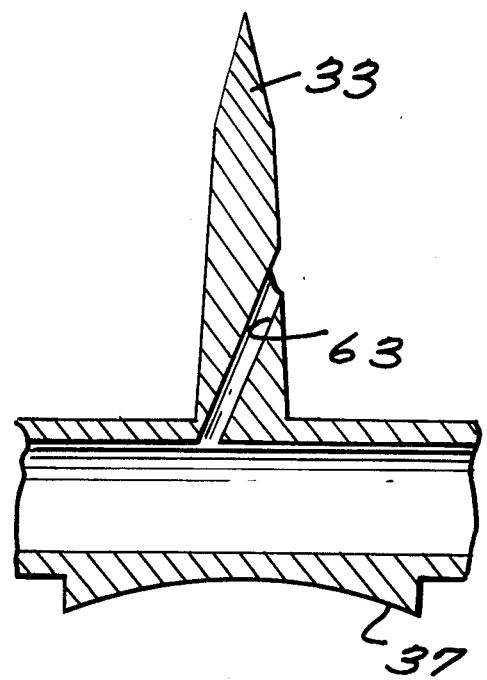

DISPENSING DEVICE FOR EXTERNAL OR INTRAVENOUS INJECTION OF FLUIDS INTO A PATIENT

BACKGROUND OF THE INVENTION

This invention relates to an improved dispensing device used for dispensing food or medicinal products by, for example, enteral and/or intravenous injection.

Containers for dispensing of medicinal products are known in the art. For example, O'Rourke disclosed in U.S. Pat. No. 1,239,947, a dispensing device comprising a bag formed of rubber having a opening at the top for receiving a fluid to be contained by the bag. At the bottom was an outlet to which tubing could be connected to permit passage of the fluid within the container to a patient. A pair of apertured nipples positioned intermediate the top and bottom of the container receive a glass tube so that an attendant can see how much fluid is in the bag and whether or not fluid is flowing out of the bag. When not in use, a pair of plugs are inserted into the nipples to prevent leakage of fluid. This type of a container is of the reusable type and has an elaborate structure which would be expensive to manufacture.

More recently, Cherkin disclosed a flexible plastic container in U.S. Pat. No. 2,704,075. In the Cherkin device, the container included a padded portion at the bottom thereof, through which a needle could be inserted into the bag to draw out fluid from the bag. The purpose for the padded material was to retain the needle in position. This container was disposable but did not provide for easy metering of fluid passing out of the container through the needle.

Accordingly, there is a need in the art for an improved dispensing device for dispensing liquid products from disposible containers for enteral and/or intravenous feeding.

SHORT STATEMENT OF THE INVENTION

This invention relates to an improved liquid dispensing device for enteral and/or intravenous injection of medicine or food into a patient. The device includes a cradle for receiving a "TETRA PAC" which is often termed a brick pack (asceptic fluid container). The brick pack includes a flexible disposable container which when emptied of its contents can be disposed. The cradle is formed of a plastic material and is designed for easy receipt of the brick pack. The cradle hangs at an angle which permits maximum delivery of the contents of the brick pack. The cradle includes a pair of apertures along its side, one near the top and one near the bottom thereof. An elongated hollow dispensing mechanism has a pair of spike projections, one near the top and one near the bottom thereof. The spike projections register with the apertures in the cradle. Each spike has an inclined channel therethrough to the hollow interior of the dispensing mechanism. The dispensing mechanism includes a scale with an adjustable marker for establishing the amount of liquid to be dispensed. At the top of the dispensing device is a vent hole which may be designed to include or form a filter mechanism. The vent hole permits the passage of air into the hollow interior of the upper dispensing member. At the bottom of the dispensing member is an outlet connectable to a tube for coupling the fluid to a patient or other device.

In operation the upper and lower spikes of the dispensing mechanism are inserted through the apertures in the cradle and pierce the walls of the brick pack positioned in the cradle. Fluid in the brick pack flows into the dispensing device to the level of the fluid in the brick pack. Air passes in through the vent at the top of the dispensing unit and into the brick pack through the upper spike. This equalizes pressure within the brick pack so that fluid can flow uniformly from the brick pack into the dispensing device and out through the outlet thereof. As the fluid leaves the brick pack, the level thereof decreases and correspondingly the level of fluid in the dispensing device decreases. This can be viewed from the graduated scale on the dispensing device. After the fluid in the brick pack has been completely drained, the dispensing device is removed and the brick pack can then be disposed and a new pack inserted in place thereof.

BRIEF DESCRIPTION OF THE DRAWINGS

Other objects, features and advantages of the present invention will become more fully understood from the following detailed description of the preferred embodiment of the present invention, the appended claims and the accompanying drawings in which:

FIG. 1 is an exploded perspective view of the preferred embodiment of the present invention;

FIG. 2 is a side elevation view of the cradle of the present invention;

FIG. 3 is a side elevation of the dispensing member of the present invention; and FIG. 4 is a section view of a spike portion of the dispensing member.

DETAILED DESCRIPTION OF THE PREFERRED EMBODIMENT

Refer now to FIG. 1 which is an exploded view of the preferred embodiment of the present invention. Illustrated is a cradle 11 which is formed of a frame having parallel side members 13 and 15 extending between a bottom end member 17 and a top end member 19. Not illustrated is a bottom member 21. At the top of the cradle is a hanger member 23 which is secured as illustrated to a top member 25. The sides, bottom, end and top members are secured to one another by techniques known in the art. For example, these parts may be glued to one another, bonded by conventional heat treating methods or selected parts may be formed integrally. The hanger member 23 is for the purpose of hanging the cradle on an i.v. pole or other such hanging device. The side member 13 has a pair of apertures 25 and 27 formed therein. These apertures being respectively located near the bottom and top of the cradle.

In use, a brick pack is positioned in the cradle as shown in dotted line form for dispensing. The brick pack may be formed of any suitable material such as, plastic or cardboard. It must be capable of being pierced by a pair of plastic spikes which pass through the apertures 25 and 27. A dispensing mechanism 29 is preferably formed of a plastic material such as A.B.S. and incudes a central hollow opening therein which extends along the length of the dispenser 29. At one side of the dispenser are a pair of spikes 31 and 33 each having an opening therethrough into the central opening in the dispenser 29. These spikes 31 and 33 pass through apertures 27 and 25, respectively, to pierce the brick pack 28 positioned in the cradle 11.

On the opposite side of the dispenser 27 are concave surfaces 35 and 36 which serve as pressure bearing areas for pushing the spikes 31 and 33 into the apertures 27 and 25, respectively. This side of the dispenser also has a graduated scale which is transparent or translucent to the fluid passing through the inner hollow opening of the dispenser 29. Accordingly, as the fluid is dispensed from the brick pack 28, the lowering level of fluid in the brick pack is displayed with respect to the graduated scale 39. As desired, an adjustable slide formed of a plastic or metallic material is positioned about the graduated scale and is in frictional engagement with a slot 41 on each side of the dispenser for movement up and down the graduated scale. The frictional engagement permits the adjustable slide 41 to be fixed at a desired location on the scale.

At the top of the dispenser is a vent opening 45 into which is positioned a cap having an aperture 49 therein. The aperture receives a circular filter 51 which permits ambient air to flow to the interior of the dispenser 29 through the aperture 49. However, the filter blocks particulate flow and other such materials which might contaminate the fluid in the dispenser. The purpose for the filter and aperture 49 at the top of the dispenser is to permit atmospheric air to enter into the brick pack 28 through the opening in the spike 31. This permits the uniform flow of fluid from the brick pack into the dispenser 29 and out through an outlet opening 51 at the bottom of the disenser. The fluid egressing from the dispenser passes through a tubular member 53 to a patient.

Refer now to FIG. 3 which is a side elevation view of the dispensing device 29 and to FIG. 4 which is a section view of a spike portion thereof. As illustrated, the spikes 31 and 33 each have an aperture 61 and 63 formed therein. The apertures are formed at an angle with respect to the spikes so that when the spike is inserted through the walls of the brick pack, particulate matter from the brick pack do not clog the openings 61 or 63. Also illustrated is the convex portions 35 and 37 and their relationships to the spikes 31 and 33. Thus, by pressing on the concave portions 35 and 37, the spikes 31 and 33 are forced through the walls of the brick pack to communicate the openings 61 and 63 with the fluid inside the brick pack.

As illustrated in FIG. 2 the hanger member 23 is formed integrally with the top 25 and upper end portion 19 of the cradle. Preferably, the hanger has a reduced cross-sectional portion 65 which permits the cradle to rotate with respect to the hanger portion 23. This permits flexibility in the hanging of the cradle and as the fluid drains from the brick pack, permits rotation of the brick pack and cradle with respect to the hanger. This permits the dispensing device 29 to maintain a constant vertical orientation thereby permitting the maximum efficient delivery of the fluid.

While in the preferred embodiment, the cradle is formed of A.B.S. plastic material. It should be appreciated that the cradle could be formed of any suitable material known in the art. In the preferred embodiment, the dispenser 29 is formed of clear polycarbonate. However, it should, also, be appreciated that the dispenser 29 can be formed of any suitable material known in the art. In this regard, of course, the portion of the dispenser along the wall having a graduated scale should be clear or at least translucent to the material inside of the dispenser.

While the present invention has been disclosed in connection with the preferred embodiment, it should be appreciated that there may be other embodiments of the invention which fall within the spirit and scope thereof as defined the appended claims.

What is claimed is:

1. A dispensing device for enteral or intravenous injection of fluids into a patient comprising:
   a cradle member for supporting a disposable aseptic rectangular package of fluid at a tilted angle so that said package has a single uppermost and lowermost location, said cradle member including a pair of side walls diagonally disposed between diagonal corners of sides on said dispensing package, said cradle side walls having uppermost and lowermost corners, said side walls being terminated in a lowermost cross member and in an uppermost cross member for interconnecting said side walls, said cross members each having horizontal and vertical portions interconnecting said side walls, said side walls and said cross members defining a truncated rectangular shaped box, a first hole formed in at least one side wall proximate said uppermost corner and a second hole formed in at least one side wall proximate said lowermost corner and a hangle fixedly secured to said upper cross member for supporting said cradle member; and
   a dispensing means for dispensing said fluid from said aseptic package, said dispensing means including means for piercing said package through said holes in said side walls to draw fluid therefrom into said dispensing means, said dispensing means further comprising an opening at the top thereof, said opening comprising an air filter for removing particulate matter from the air entering said dispensing means, and
   means for indicating the level of fluid in said package.

2. The dispensing device of claim 1 wherein said dispensing means includes a hollow interior portion for receiving fluid from said package, said fluid rising in said hollow interior to the level of said fluid in said package; and said means for indicating comprises a graduated scale.

3. The dispensing device of claim 1 wherein said cradle member further comprises means for maintaining said cradle and said dispensing means in a vertical orientation.

4. A dispensing device of claim 3 wherein said maintaining means comprises a reduced cross section portion between said handle and said cradle member for maintaining said cradle and said dispensing means in a vertical orientation.

5. The dispensing device of claim 1 wherein said means for piercing comprises a pair of spikes, one each positioned approximate the top and bottom of the dispensing member, said spikes having a channel therethrough for permitting the egress of fluid from said package through said channel into said dispensing means and for permitting the egress of air from the dispensing means into said package.

6. The dispensing device of claim 5 wherein said channels through said spikes are at an oblique angle with respect to the longitudinal axis of said spikes so that particles from said package do not clog said channels into said dispensing means.

7. The dispensing device of claim 6 wherein said means for indicating comprises a scale on said dispensing means and a scale marker selectively positionable along the scale of said dispensing means for indicating when a predetermined amount of fluid has been dispensed.

8. A dispensing device for enteral or intravenous injection of fluids into a patient comprising:
- a cradle member for supporting a disposable rectangular package of aseptic fluid at a tilted angle so that said fluid has a single uppermost and a single lowermost location, said cradle having a pair of side walls diagonally disposed between diagonal corners of sides on said package and terminated in an uppermost and an lowermost cross member, each cross member having a generally vertically portion and a generally horizontally portion, said side walls and cross members defining a support for receiving an retaining said package of fluid, a first hole being formed in at least one side wall proximate said uppermost cross member a second hole being formed in at least one side wall proximate said lowermost cross member, and a handle fixedly secured to said upper cross member for supporting said cradle member;
- a dispensing means for dispensing said aseptic fluid from said package, said dispensing means including means for piercing said package at said uppermost and said lowermost locations to draw fluid therefrom into said dispensing means, said piercing means comprising a pair of spikes, one each positioned proximate the top and bottom of said dispensing member, said spikes having a channel therethrough for permitting the egress of fluid from said package through said channel into the bottom of said dispensing means and for permitting the ingress of air from the top said dispensing means into said package,
- means for conveying said fluid from said bottom of said dispensing means to a patient, and
- means for indicating the level of fluid in said package.

9. A dispensing device of claim 8 wherein said dispensing member includes a hollow interior portion for receiving fluid from said package, said fluid rising in said hollow interior to the level of said fluid in said package, and said means for indicating comprises a graduated scale; and
- an opening in the top of said dispensing member, said opening comprising an air filter for removing particulate matter from the air entering the dispensing member.

10. A dispensing device of claim 9 wherein said handle includes a reduced cross-section portion for maintaining said package tilted with said first and second holes in said side walls proximate the uppermost and lowermost locations respectively.

11. A dispensing device according to claim 9 wherein said side walls of said cradle member are integrally formed with said uppermost crossmember.

* * * * *